(12) United States Patent
Pichon et al.

(10) Patent No.: US 6,860,870 B2
(45) Date of Patent: Mar. 1, 2005

US006860870B2

(54) SELF-CLEANING FLUID DELIVERY DEVICE FOR MEDICAL APPLICATIONS

(75) Inventors: Dean M. Pichon, Arlington, MA (US); David J. Nedder, Attleboro, MA (US); John R. Sousa, Littleton, MA (US); J. Jeffrey Kablik, Tyngsboro, MA (US); Albert H. Linder, Hagen (DE)

(73) Assignee: Focal, Inc., Lexington, MA (US)

( * ) Notice: Subject to any disclaimer, the term of this patent is extended or adjusted under 35 U.S.C. 154(b) by 20 days.

(21) Appl. No.: 10/034,836

(22) Filed: Dec. 21, 2001

(65) Prior Publication Data

US 2002/0198564 A1 Dec. 26, 2002

Related U.S. Application Data (63) Continuation of application No. 09/801,097, filed on Mar. 7, 2001, now abandoned, which is a continuation of application No. PCT/US99/21521, filed on Sep. 17, 1999.
(60) Provisional application No. 60/100,718, filed on Sep. 17, 1998.

(51) Int. Cl.[7] .............................................. A61M 5/00
(52) U.S. Cl. ....................... 604/191; 604/82; 604/187; 604/118; 604/121; 604/119; 604/173; 222/135; 222/386.5; 222/630; 222/389; 222/263; 606/213
(58) Field of Search ................................. 604/191, 236, 604/187, 82, 232, 266, 269, 21, 30, 33, 34, 43, 118, 121, 119, 173, 23–26, 20, 213–215; 222/135, 136, 386.5, 630, 4, 389, 388, 263; 239/290, 432, 311, 303, 322, 337, 338, 340, 341, 346, 349, 364, 365, 371; 424/78.08; 118/300, 302

(56) References Cited

U.S. PATENT DOCUMENTS

| | | | |
|---|---|---|---|
| 4,037,599 A | | 7/1977 | Raulerson |
| 4,040,420 A | | 8/1977 | Speer |
| 4,179,068 A | | 12/1979 | Dombrowski |
| 4,180,239 A | | 12/1979 | Valukis |
| 4,329,988 A | | 5/1982 | Sarnoff et al. |
| 4,359,049 A | | 11/1982 | Redl et al. |
| 4,487,365 A | * | 12/1984 | Sperber ........................ 239/8 |
| 4,610,666 A | | 9/1986 | Pizzino |

(List continued on next page.)

FOREIGN PATENT DOCUMENTS

| | | |
|---|---|---|
| EP | 0 037 393 A1 | 10/1981 |
| EP | 0 041 022 A1 | 12/1981 |

(List continued on next page.)

OTHER PUBLICATIONS

Ogawa, Jun–ichi, et al., "Newly Devised Instrument for Spraying Aerosolized Fibrin Glue in Thoracoscopic Operations", *Ann. Thorac. Surg.*, vol. 55, 1993, pp. 1595–1596.

*Primary Examiner*—Nicholas D. Lucchesi
*Assistant Examiner*—Cris L. Rodriguez
(74) *Attorney, Agent, or Firm*—Wolf, Greenfield & Sacks (57) ABSTRACT

A gas powered spraying device that can be used for single or multi-part reactive medical polymer compositions is provided. A fluid or one or more reactive solutions are sprayed independently at a tissue surface, and the spraying of each solution of multi-component embodiments is controlled by a separate valve. Each solution is provided with a separate spray outlet, and each spray outlet is surrounded by an annular sheath of flowing gas. Gas flow is provided at two or more flow levels, including a high level flow for active spraying and a low level bypass flow to remove drips and prevent clogging, which can improve device reliability. Gas pressure can be used to drive fluid to its spray outlet, as well as to spray the fluid from the outlet to the tissue surface.

62 Claims, 5 Drawing Sheets

U.S. PATENT DOCUMENTS

| | | |
|---|---|---|
| 4,631,055 A | 12/1986 | Redl et al. |
| 4,673,395 A | 6/1987 | Phillips |
| 4,735,616 A | 4/1988 | Eibl et al. |
| 4,740,203 A | 4/1988 | Hoskins et al. |
| 4,874,368 A | 10/1989 | Miller et al. |
| 4,978,336 A | 12/1990 | Capozzi et al. |
| 4,979,942 A | 12/1990 | Wolf et al. |
| 5,022,563 A | 6/1991 | Marchitto et al. |
| 5,104,375 A | 4/1992 | Wolf et al. |
| 5,116,315 A | 5/1992 | Capozzi et al. |
| 5,149,330 A | 9/1992 | Brightbill |
| 5,226,877 A | 7/1993 | Epstein |
| 5,322,510 A | 6/1994 | Lindner et al. |
| 5,344,078 A * | 9/1994 | Fritz et al. .................. 239/296 |
| 5,368,563 A | 11/1994 | Lonneman et al. |
| 5,470,311 A | 11/1995 | Setterstrom et al. |
| 5,474,540 A | 12/1995 | Miller et al. |
| 5,499,745 A * | 3/1996 | Derian et al. ............... 222/136 |
| 5,505,712 A | 4/1996 | McMillian |
| D376,376 S | 12/1996 | Tourigny et al. |
| 5,582,596 A | 12/1996 | Fukunaga et al. |
| 5,605,541 A | 2/1997 | Holm |
| 5,612,050 A | 3/1997 | Rowe et al. |
| 5,665,067 A * | 9/1997 | Linder et al. .................. 604/82 |
| 5,698,189 A | 12/1997 | Rowe et al. |
| 5,738,728 A * | 4/1998 | Tisone ........................ 118/638 |
| 5,748,968 A | 5/1998 | Nally et al. |
| 5,749,968 A | 5/1998 | Melanson et al. |
| 5,759,169 A | 6/1998 | Marx |
| 5,759,171 A | 6/1998 | Coelho et al. |
| 5,800,373 A | 9/1998 | Melanson et al. |
| 5,874,500 A | 2/1999 | Rhee et al. |
| 6,059,749 A * | 5/2000 | Marx .......................... 604/82 |
| 6,063,055 A * | 5/2000 | Epstein et al. ................. 604/82 |
| 6,179,862 B1 * | 1/2001 | Sawhney .................... 606/214 |
| 6,325,853 B1 * | 12/2001 | Hogan et al. ................ 118/300 |
| 6,613,020 B1 * | 9/2003 | Holm et al. ................. 604/191 |
| RE38,281 E * | 10/2003 | Tisone ........................ 422/100 |

FOREIGN PATENT DOCUMENTS

| | | |
|---|---|---|
| EP | 0 105 493 A2 | 4/1984 |
| EP | 0 156 098 A2 | 10/1985 |
| EP | 0 249 186 A1 | 12/1987 |
| EP | 0 315 222 A2 | 5/1989 |
| WO | WO 90/01959 A1 | 3/1990 |
| WO | WO 91/07197 A1 | 5/1991 |
| WO | WO 96/29370 A2 | 9/1996 |
| WO | WO 96/40797 A1 | 12/1996 |
| WO | WO 97/36622 A1 | 10/1997 |
| WO | WO 98/20931 A1 | 5/1998 |
| WO | WO 99/34833 A1 | 7/1999 |

* cited by examiner

SELF-CLEANING FLUID DELIVERY DEVICE FOR MEDICAL APPLICATIONS

This application is a continuation of U.S. application Ser. No. 09/801,097, filed Mar. 7, 2001, now abandoned which is a continuation of International Patent Application Serial No. PCT/US99/21521, filed Sep. 17, 1999, which claims priority to U.S. provisional patent application Ser. No. 60/100,718, filed Sep. 17, 1998.

FIELD OF THE INVENTION

This invention relates generally to a medical device for delivering a fluid to a tissue surface, and more particularly to a gas-powered self-cleaning sprayer for application of a fluid or a multi-part reactive polymer system to tissue for medical uses.

BACKGROUND OF THE INVENTION

There are many devices disclosed or proposed in the art for the application of medical materials by spraying. A particular field of spray application is for multi-part reactive materials, particularly for two-part medical materials, in which one part ("A") is reactive with another part ("B") either directly on contact, or upon passage of time, or upon activation, such as by heat or light. An important subfield of such applicators is dedicated to the application of fibrin sealant, in which part A contains fibrinogen, part B contains thrombin, and at least one part contains a calcium salt. On contact between the solutions, the fibrinogen is cleaved by the calcium-activated thrombin, and fibrin is formed. The fibrin self-assembles into a rigid structure, as occurs in blood clotting. This system is used to apply sealing coatings to the body, and to adhere tissue together where the mechanical stress is low. To achieve the desired effect, the two parts of the system must be intimately mixed during application to the tissue, but must be kept separate until that time. Exemplary devices for delivery of two separate fluids to a tissue surface are described in U.S. Pat. No. 5,582,596 to Fukunaga et. al., and U.S. Pat. No. 5,665,067 to Linder et. al. Linder describes a delivery device with a pair of fluid outlets surrounded by a single air annulus for spraying. Fukunaga describes a device with outlets with separate annuli, designed specifically for application of biocompatible adhesive containing human or animal protein, such as fibrin sealant, to a surgical site. The device of Fukunaga includes liquid outlets that extend distally beyond gas nozzles that surround the outlets, which Fukunaga states ensures that solutions ejected from the outlets will be sprayed uniformly by gas emitted form the nozzles.

Fibrin sealant systems can have numerous limitations, including the possible presence of viruses and prions, and newer all-synthetic systems have been devised which can alleviate these and other problems. It is easier and more reliable to tailor the mechanical properties of a synthetic system, and each of strong adherence to tissue, biocompatibility and flexibility of a coating can be achieved. An example of such a system is described in U.S. Pat. Nos. 5,749,968 and 5,800,373 and in international patent publication no. WO 96/29370. In this system, a solution of a reactive water-soluble macromer, such as a polyethylene glycol molecule extended with biodegradable groups such as lactide and made reactive by end capping with acrylate, is reacted with light in the presence of a photoinitiator or photosensitizer, and covalently polymerizes into a hydrogel. As disclosed in U.S. Pat. No. 5,748,968, it has been found that such a prior art hydrogel will adhere more strongly to tissue if the tissue is first coated with at least a part of an initiation system (herein, a "primer" or priming solution.) During polymerization, the tissue-adherent initiator assures satisfactory reaction and mechanical bonding at the tissue surface. In U.S. Pat. No. 5,800,373, it is demonstrated that this system can be further enhanced by incorporating a chemically reactive ("redox") initiation system along with a photoinitiation system. Then one component of the redox system is used in the primer, and the other in the bulk, macromer-containing solution.

In these systems, and with other chemistries (e.g. as discussed in U.S. Pat. No. 5,874,500 and international patent publication no. WO 99/34833) it is often important to apply two or more fluids independently, and in some cases sequentially, to a tissue surface. Even where only one fluid is applied, it can be important to apply the fluid evenly, conveniently, and cleanly. It can also be desirable to apply the solutions in variable ratios. It can also be important to prevent any reaction of the two components in the device before the application is completed, to prevent having to clean or replace the application device during a medical procedure. It is an object of the invention to provide improved medical fluid delivery devices to address these and other needs.

SUMMARY OF THE INVENTION

The present invention provides devices that use pressurized medical gas for spraying fluid to a tissue surface. In one embodiment, a device provides a constant flow of gas to provide a self-cleaning action at the liquid outlet of the device. The device can have one or more outlets. A preferred embodiment of the invention is a device which can deliver more than one material, simultaneously or sequentially, to one or more of a tissue surface and the surface of a medical device. The materials can be reactive upon mixing.

In the device of the invention, as more fully described herein, fluids comprising one or more components of a biocompatible tissue coating material are expressed through outlets of the device. The preferred motive force for expressing a liquid is pressurization of a reservoir, which is preferably carried on the device. The pressurization is preferably arranged so that delivery of the fluid is not affected by the orientation of the application device. Pressurization of the fluid(s) can be effected by the same source of gas used to spray fluid to the tissue surface. Fluid is expressed from an outlet, in preferred embodiments surrounded by an annulus through which pressurized gas flows. Preferably, each reactive component is surrounded by a separate annulus, to prevent mixing of reactive components on or in the device itself. Also in preferred embodiments, the rate of gas flow supplied for spraying fluid against tissue is at controlled to be at a high rate for spraying or at a low rate for keeping orifices clean. Furthermore, in preferred embodiments, conduits carrying biocompatible tissue coating material do not protrude substantially beyond a surface of the device at which they emerge, to prevent these often small and needle-like conduits from catching on tissue.

In one aspect, the invention is a series of devices. One device for applying a biocompatible agent to a tissue surface includes a housing having a biocompatible agent conduit connectable to a source of a biocompatible agent. The conduit includes a biocompatible agent outlet adapted to emit a biocompatible agent. The housing has a gas conduit that is connectable to a source of a pressurized medical gas with an outlet adapted to emit pressurized medical gas in an orientation that carries biocompatible agent from the biocompatible agent outlet to a tissue surface. A gas regulator is provided that can provide medical gas to the outlet of the gas conduit at at least two predetermined positive gas pressures actuator.

Another device of the invention includes a reservoir of a biocompatible agent that is connectable to a source of a pressurized gas, and a housing with a biocompatible agent conduit connectable to the biocompatible agent reservoir. The housing includes a biocompatible agent outlet adapted to emit an agent to a tissue surface. The housing also includes a gas conduit that is connectable to a source of a pressurized medical gas with a gas outlet adapted to emit pressurized medical gas in an orientation that carries biocompatible agent from the outlet of the biocompatible agent conduit to a tissue surface.

Another device of the invention includes a housing having at least two biocompatible agent conduits each connectable to a source of a biocompatible agent and each including a biocompatible agent outlet adapted to emit a biocompatible agent. The housing has at least two gas conduits, each of which is connectable to a source of a medical gas at a pressure greater than atmospheric pressure. Each gas conduit has a separate gas outlet associated with one of the at least two biocompatible agent outlets, adapted to emit pressurized medical gas in an orientation carrying biocompatible agent from a biocompatible agent outlet to a tissue surface. The biocompatible agent outlets and the gas outlets define together at least two agent/gas delivery outlets integral with a surrounding surface of the device defining a planar area greater than at least twice the cross sectional area of the agent/gas delivery outlets.

Another device of the invention for the application of a coating to a tissue surface of a patient includes a fluid inlet port configured to connect to a source of a fluid, a gas inlet port configured to connect to a source of pressurized medical gas, a fluid delivery outlet, and a fluid conduit fluidly connecting the fluid delivery outlet with the fluid inlet port, a valve associated with the fluid conduit able to regulate the outflow of fluid from the fluid delivery outlet, a gas outlet proximate the fluid delivery outlet, and a gas conduit fluidly connecting the gas outlet with the gas port, and means for regulating the rate of gas flow through the gas outlet wherein, while said device is in operation, gas flow is maintained at a flow level sufficient to remove any fluid present at the fluid delivery outlet.

Another aspect of the invention provides a series of methods and uses. One method involves applying gas pressure to a biocompatible agent thereby urging the agent through an orifice, and applying the agent urged through the orifice to a tissue surface by directing a flow of a medical gas at the agent and carrying the agent from the orifice to the tissue surface with the gas flow.

Another method of the invention involves applying a biocompatible agent to a tissue surface by carrying the agent from an outlet of a conduit to the tissue surface with a medical gas provided at a first pressure, ceasing application of the agent to the tissue surface, and clearing any residual biocompatible agent from the outlet by directing the medical gas proximate the outlet at a second pressure less than the first pressure.

Another method of the invention involves emitting a biocompatible agent from an outlet of a conduit with a medical gas provided at a first pressure, ceasing emission of the agent, and clearing any residual biocompatible agent from the outlet by directing the medical gas proximate the outlet at a second pressure less than the first pressure.

Uses of the devices of the invention also are part of the invention.

Other advantages, novel features, and objects of the invention will become apparent from the following detailed description of the invention when considered in conjunction with the accompanying drawings, which are schematic and which are not intended to be drawn to scale. In the figures, each identical or nearly identical component that is illustrated in various figures is represented by a single numeral. For purposes of clarity, not every component is labeled in every figure, nor is every component of each embodiment of the invention shown where illustration is not necessary to allow those of ordinary skill in the art to understand the invention.

DETAILED DESCRIPTION

Definitions:

The words "comprising", "consisting of" and "consisting essentially of" are intended to be construed as they are used in the U.S. Manual of Patent Examining Procedure on the filing date of this application "including" and "having" are to be interpreted to mean "comprising", i.e. including, but not limited to.

The word "fluid" is meant to include any of gasses, liquids, powders, or a combination. Liquids may be of any viscosity except as otherwise specified, and may exhibit any known non-Newtonian effects known in the art, such as thixotropy, rheopexy, and a behavior as a solid or semi-solid material below a threshold stress.

The word "coating" is used herein to include the result of essentially any application of fluid to a tissue surface, and includes without limitation thin coatings, hydrogel coatings, selective barriers (e.g. barriers to liquid permutation, adhesion barriers, etc.), adhesives, sealants and polymeric supports, when formed on or between tissue or a tissue-contacting surface by the devices and methods of the invention. A "multi-part" coating comprises at least two species that remain separated until application a target tissue site, e.g. two reacting species which must remain separated until application to the target site at which point reaction takes place.

In describing devices of the invention, the words "distal" and "proximal" shall be determined, if not otherwise clear, in terms of fluid flow within the device. The fluids are emitted from the device's distal portion, while the fluid sources are located proximally to that point.

In the following description that accompanies the drawings, a specific set of devices and controls is described including two reservoirs of biocompatible agents that are driven through the device to outlets via gas pressure, specifically via pressure from the same source of medical gas that is directed at the outlets to spray the agent onto tissue. It is to be understood that these embodiments are exemplary only. For example, any number of reservoirs, including but a single reservoir, can be used. Biocompatible agent can be driven from the reservoirs and through the device via conventional techniques such as manually-driven plungers, in some embodiments. The device can include any number of biocompatible agent conduits, including a single conduit carrying a mixture of biocompatible agents from separate reservoirs, or separate conduits that maintain biocompatible agents separate from each other until delivery from device outlets. The device can include, or can be free of, an emitter of energy directable at agent emitted from the device onto a tissue surface. The invention is defined by essentially any permutation of a variety of advantageous features described herein and in the accompanying claims.

Figure 1:
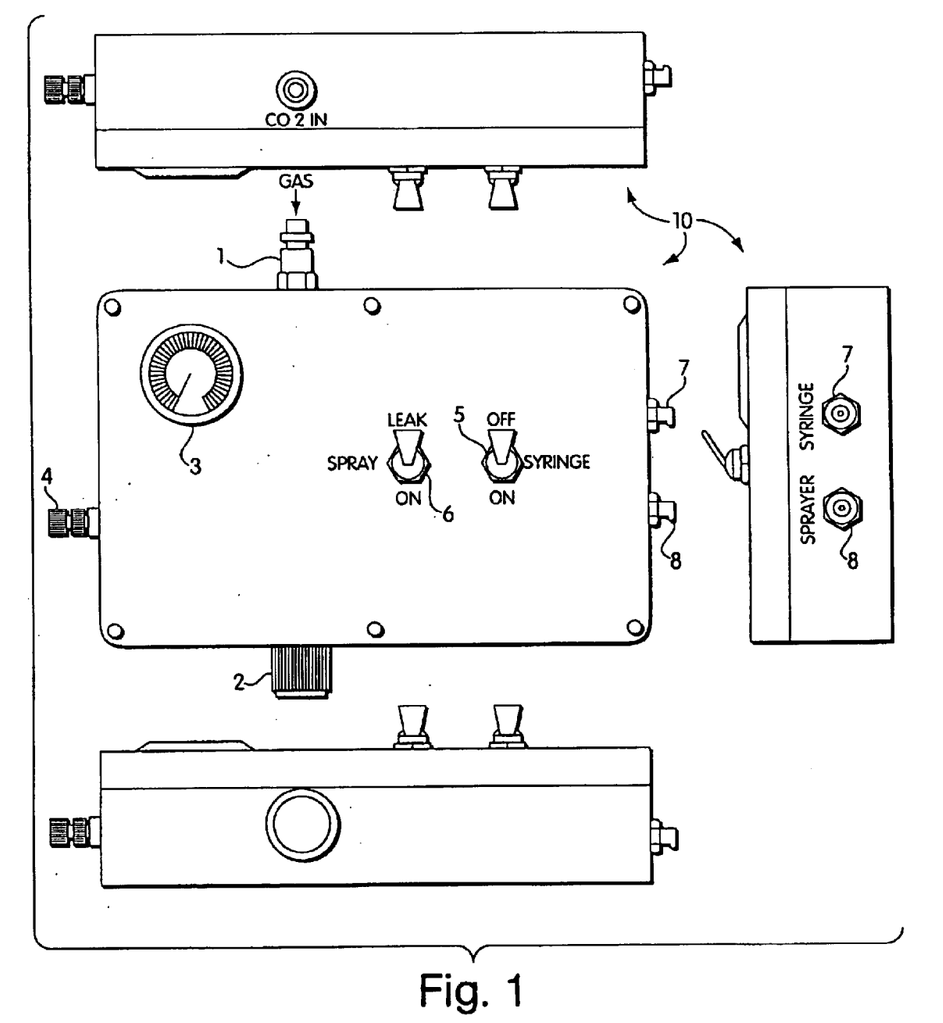
FIG. 1 illustrates a control box for use with devices of the invention.

Referring to FIG. 1, a control box 10, for use in connection with devices of the invention, is shown in four views of its exterior. Control box 10 includes a connector 1 for connection to a source of a medical gas, a pressure regulator 2 and associated pressure gauge 3, and a needle valve 4 for regulation of bypass gas flow which determines a "low", or self-cleaning, gas flow rate, as described more fully below. A toggle 5 controls gas pressure applied to a reservoir or reservoirs of fluid to be sprayed onto a tissue surface. Another toggle 6 switches gas flow rate from a low, self-cleaning value ("leak") to a high value for spraying ("on"). Toggles 5 and 6 are connected to gas outlets 7 and 8, respectively, to control reservoir ("syringe") pressurization and sprayer gas flow level, respectively. These outlets can be connected to appropriate inlets of devices of the invention shown in subsequent figures by flexible plastic tubing (not shown).

Figure 2:
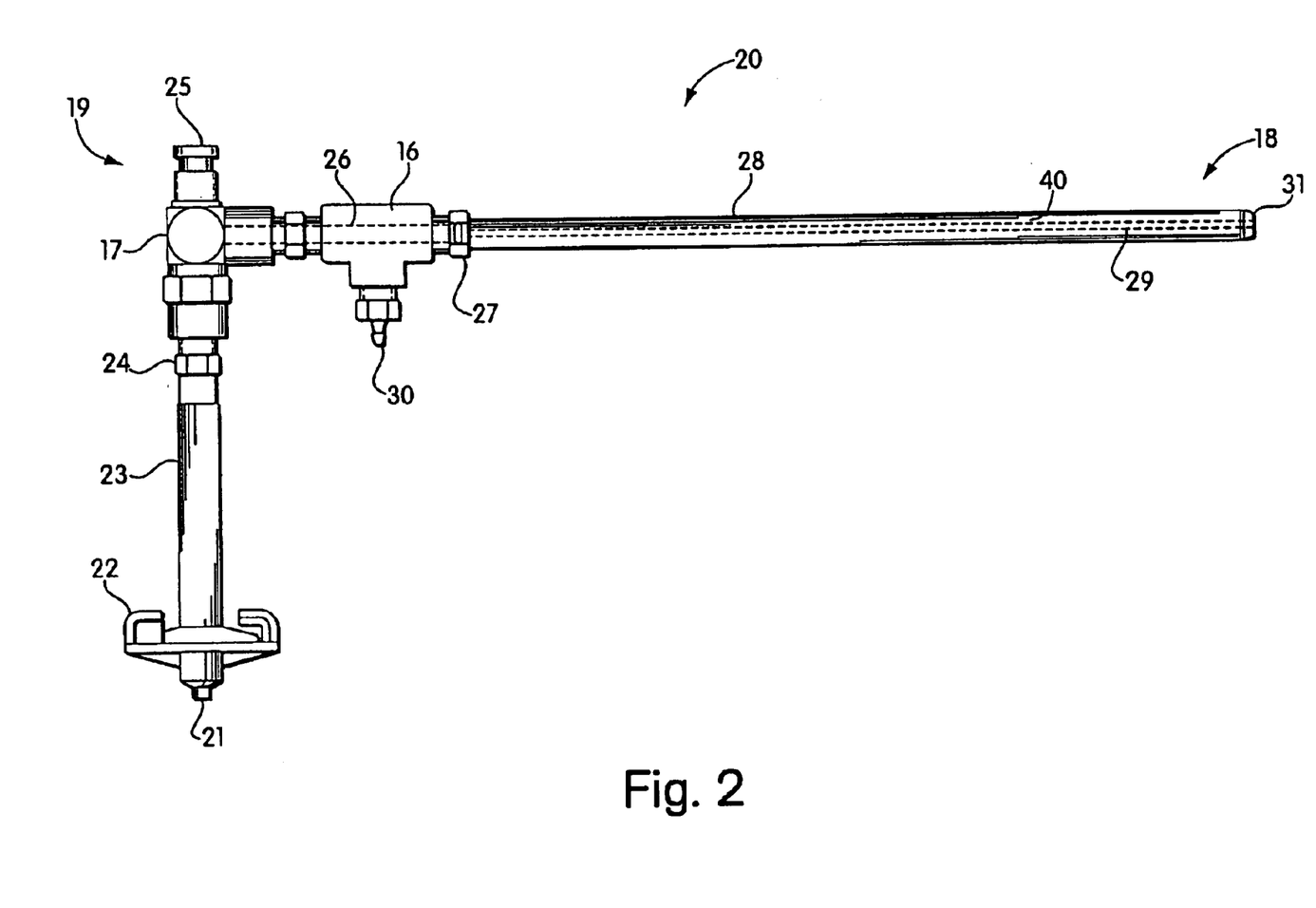
FIG. 2 illustrates a medical spray device according to one embodiment of the invention.

FIG. 2 shows a side view of a delivery device 20 according to one embodiment of the invention, in which syringe barrels constitute the reservoirs of fluid for delivery to a tissue surface. Device 20 includes a handle defined by a pair of vertically-oriented syringe barrels (only one syringe barrel 23 is shown in this side view) at a proximal end 19 thereof and a coupler 17 constructed to receive the syringe barrels. Coupler 17 receives the upward-pointing barrels and contains fluid passageways directing fluid flow horizontally for connection with a unit 16. Unit 16 includes a gas inlet and is connectable to a nozzle housing assembly 28.

Gas pressure enters the syringes at a nipple 21 on each of two syringe barrel pressurization adapters 22 which are locked to the proximal end of each syringe barrel. Nipples 21 are connectable to tubing connected to outlet 7 of FIG. 1. A slidable sealing piston, or septum, is provided inside each syringe barrel (not shown), fluid to be delivered is positioned between the piston and the distal end of the syringe, and pressurized gas fills space between the piston and the proximal end of each syringe. The distal end of each syringe connects to a fluid inlet of coupler 17 via a Luer-lock connection 24.

A pair of valve actuators (buttons, or triggers; one actuator 25 is shown) protrude from the top of coupler 17 and connect to a pair of valves (not shown in FIG. 2) in coupler 17 for regulation of fluid flow from each of the pressurized syringe barrels to conduits within housing 28. When actuator 25 is depressed, a valve opens to allow fluid to pass into the body of the device (coupler 17 and unit 16), and the fluid is carried through passageways within coupler 17 and unit 16 to a connector 27 that connects unit 16 with housing assembly 28, and into tubes within assembly 28. At the connector, passageways in unit 16 that connect to the syringes mate to corresponding tubes in the nozzle housing assembly 28, which may be detachable. One tube 29 within housing 28 connecting to syringe 23 is shown.

Components of the invention can be made of any medically-acceptable materials suitable for sterilization, as would be recognized by those of ordinary skill in the art. Construction of the device so that some portions are inexpensive and disposable is also contemplated. In the embodiment shown, the extended housing assembly has an outer diameter of about 7 mm and a length of about 20 cm, and is made entirely of metal except for certain connecting parts in the vicinity of connector 27, which can be made of nylon, brass, or the like. Epoxy can be used to make permanent connections. The elongated distal portion (housing assembly 28) of the assembly is suitable for use through the cannula of a trocar in minimally invasive surgical procedures.

Pressurized gas from sprayer outlet 8 (FIG. 1) of the control box also enters the device at nipple 30 of unit 16. Nipple 30 is connected to a pressurized gas space 40 surrounding liquid-conveying tubing segments 26 and 29 within unit 16 and housing assembly 28, respectively. Fluid (s) from the syringe(s) and gas from pressurized gas space 40 surrounding tube 29 within housing 28 are emitted from the device from spray outlet face 31 at the distal end of the device.

Figure 3:
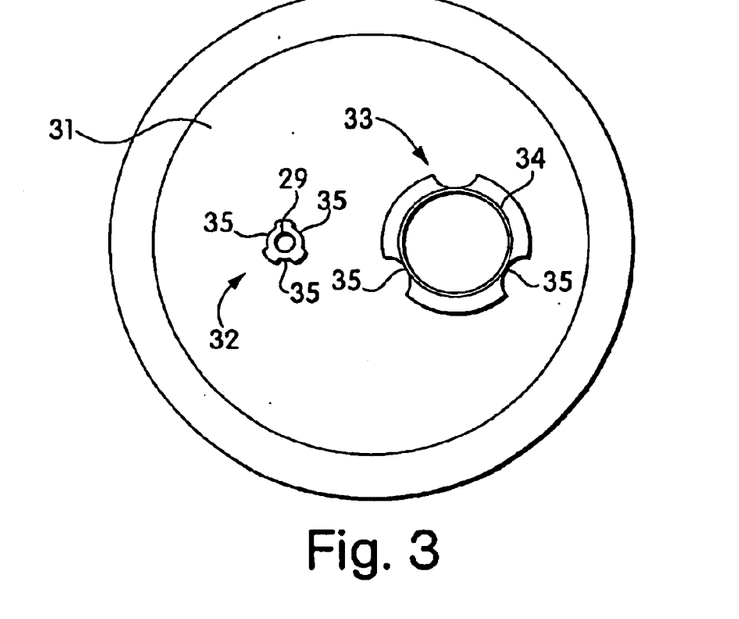
FIG. 3 illustrates a face-on view of the distal end face of the device of FIG. 2.
Figure 4:
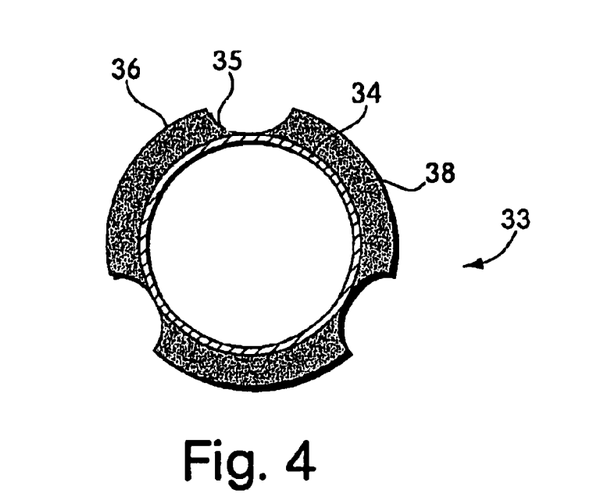
FIG. 4 illustrates an enlarged view of an aperture of FIG. 3.

FIG. 3 shows a face-on view of the distal end face (spray outlet face) 31 of device 20. Distal end face 31 includes two apertures 32 and 33. Aperture 32 contains the terminal, distal end of tube 29, and connects to syringe 23. Aperture 33 contains the terminal, distal end of a tube 34 hidden by tube 29 in FIG. 2, which connects to a syringe hidden by syringe 23. The fluid outlets of tubes 29 and 34 within housing 28 enter the apertures and are held by three projections 35 so that the outer diameter of the tubing is centered within the apertures. FIG. 4 shows an enlarged view of aperture 33. Annulus 38 (shaded) for ejection of gas from gas space 40 of housing 28 is created by the gap between the outer diameter of tube 34 and the inner edge 36 of the aperture. A similar aperture is defined surrounding the outlet of tube 29.

Tubes 29 and 34, as shown, are of different diameters. It is to be understood that the devices of the invention can carry one or any number of tubes and, where multiple tubes exist, tubes of varying diameter can be used for a variety of purposes. The device as shown is particularly suitable for use with two liquids that differ markedly in viscosity and in amount to be supplied. The smaller tube 29, for example, is suitable for carrying "primer", a low viscosity fluid containing about 30% reactive synthetic macromer of low molecular weight and certain initiators of polymerization, for application in small amounts to tissue or other surface. The larger tubes 34 is suitable for carrying "sealant", containing about 20% of a reactive macromer of higher molecular weight, as well as initiators, with relatively higher viscosity. In many cases it is desirable to apply more sealant than primer, for example two to three times as much sealant as primer, to build up a thicker layer of hydrogel having desirable mechanical properties.

Figure 5:
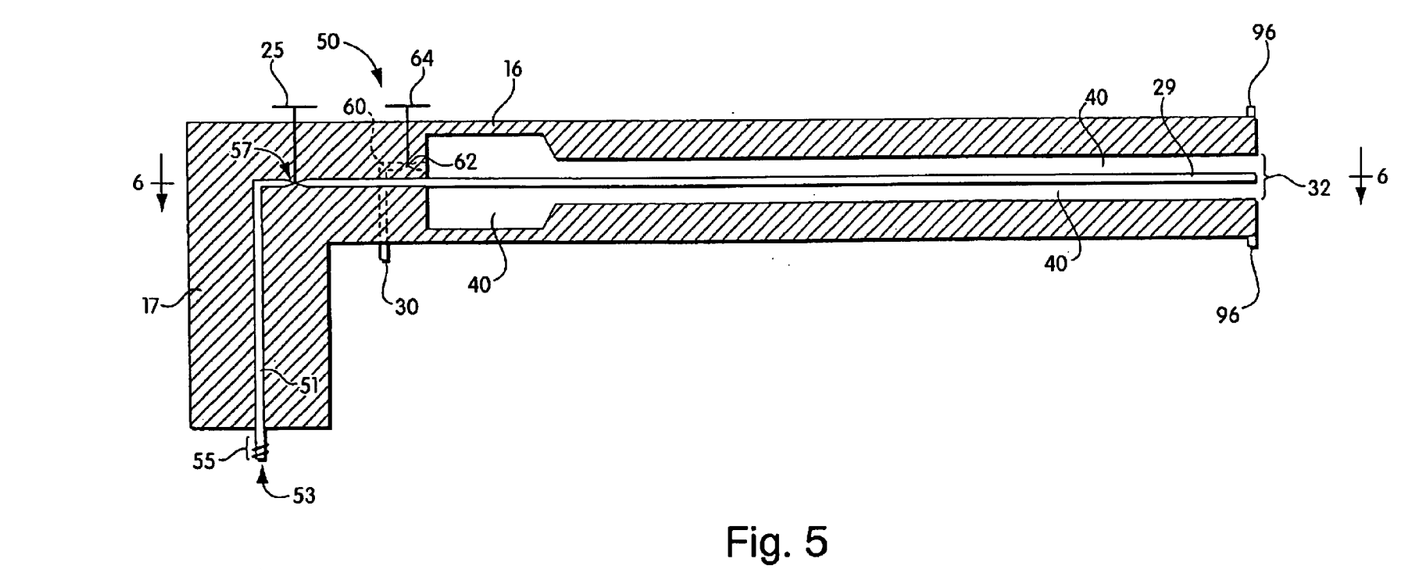
FIG. 5 is a schematic cross-sectional representation of a device similar to that of FIG. 2.

Referring now to FIG. 5, a schematic, cross-sectional view of a device 50, similar to device 20 of FIG. 2, is shown.

Device 50 includes a coupler 17, which serves as a handle at the proximal end thereof which contains a fluid passageway 51 joined to a fluid inlet 53 having a Luer lock connector portion 55 for connection to a syringe barrel. Passageway 51 extends vertically upward and then horizontally within coupler 17 and meets a valve 57, described above, operated by actuator 25 which opens and closes valve 57. Passageway 51 extends horizontally toward the distal end of the device, becoming passageway 29, as described above. Within unit 16, gas space 40 which annularly surrounds fluid passageway 29 is supplied by gas conduit 60 connected to gas inlet nipple 30. Gas conduit 60 is separated from gas space 40 by a valve 62, in the embodiment illustrated, controlled by actuator 64. Valve 62 can be an on-off valve, can be a valve that toggles between two positive gas flows, specifically a "high" gas flow and a "low" gas flow, or a three-way valve toggling between off, "low", and "high" gas flow.

Figure 6:
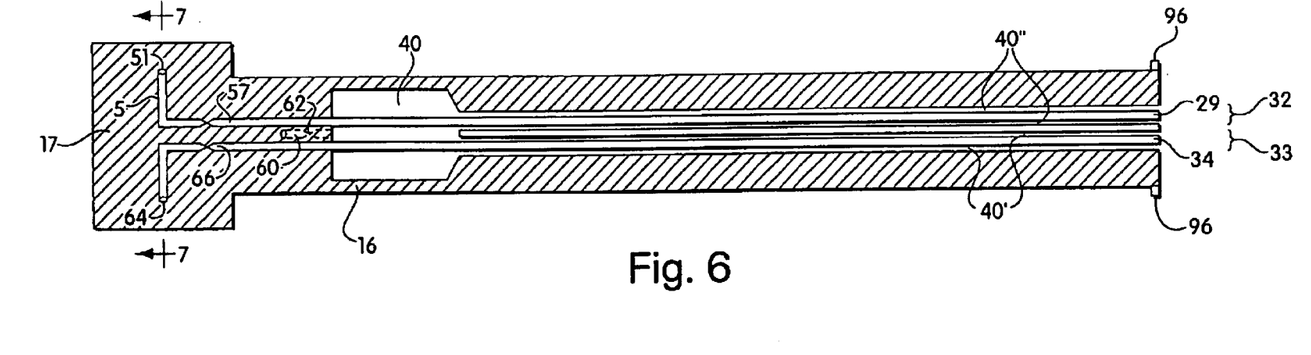
FIG. 6 is a cross-sectional view through line 6—6 of FIG. 5.

Referring now to FIG. 6, a schematic, cross-sectional view through lines 6—6 of FIG. 5 is shown. In addition to the components illustrated in FIGS. 2–5, FIG. 6 shows an additional horizontal biocompatible fluid delivery passageway 34, connecting to a vertical supply conduit 64 and separated from conduit 64 by a valve 66 similar to valve 57. Valves 57 and 66 can be controlled independently by independent actuators, or can be controlled together by a single actuator or separate actuators linked to operate as one.

Gas space 40, in one embodiment (not shown) is a single gas space that surrounds both fluid conduits 29 and 34. In preferred embodiments, such as that illustrated in FIG. 6, gas space 40 separates into two separate gas conduits 40' and 40" annularly surrounding fluid passageways 34 and 29, respectively, and together with the fluid passageways defines annular apertures 33 and 32, respectively. One advantage of a separate gas conduit for each of the separate fluid conduits is that gas pressure specifically tailored for a particular fluid and/or conduit can be used, i.e. the pressures within conduits 40' and 40" can be different. This is accomplished in the present invention by providing regulators such as constrictions or valves (not shown) in one or both of conduits 40' or 40", or other well-known techniques. Fluids of differing viscosity can sometimes be better entrained in a flow of pressurized gas to create a spray where the gas pressure is selected specifically for each fluid's viscosity. Similarly, different sized fluid delivery outlets may be better served by different gas pressures. Additionally, uniformity and/or control of spray application to tissue can be improved by providing a gas conduit outlet immediately surrounding a fluid conduit outlet, which can be achieved in the case of multiple fluid outlets with separate gas outlets for each fluid outlet.

Figure 7:
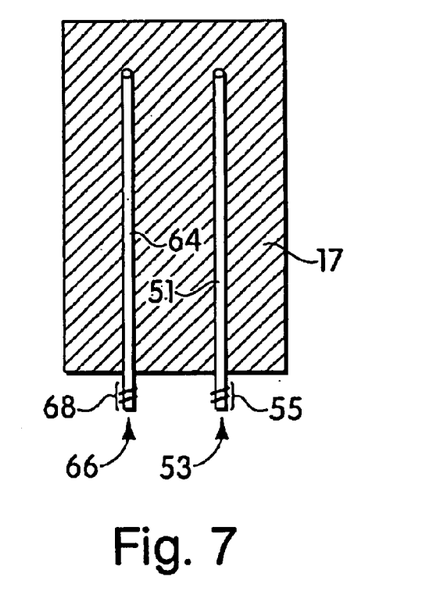
FIG. 7 is a cross-sectional view through line 7—7 of FIG. 6.

FIG. 7 is a schematic, cross-sectional view through lines 7—7 of FIG. 6, inverted, and shows fluid conduits 51 and 64. Inlet 66 of fluid conduit 64 also is shown including Luer lock connector section 68.

As shown in FIGS. 2, 5, and 6, it can be seen that each of the fluid delivery outlets 29 and 34 defines the inner boundary of a separate partial or complete annulus. An annular gas outlet is proximate each fluid delivery outlet (specifically, surrounds each) and the fluid outlet/gas outlet combination in each case defines a substantially annular, coaxial fluids/gas delivery outlet. The outlet is flush, or integral with a surrounding surface of the device defining a planar area across the face of the device that is greater than at least twice the cross-sectional area of the fluid/gas delivery outlet, i.e., the fluid conduit preferably does not protrude from the distal face of the device. Where the outlet protrudes it can define small, needle-like arrangement that can snag or tear tissue.

Figure 8:
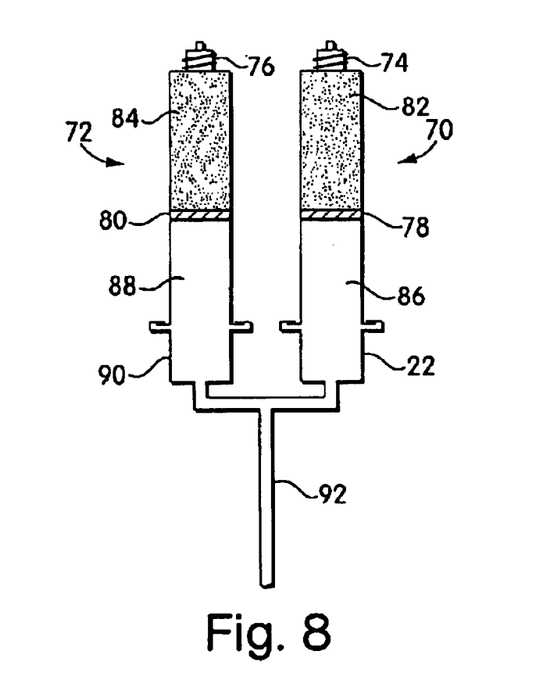
FIG. 8 is a schematic, cross-sectional view of a pair of biocompatible agent reservoirs connected to apparatus for applying gas pressure to the reservoirs, the reservoirs connectable to the apparatus of FIGS. 2 and 5–7.

FIG. 8 is a cross-sectional schematic illustration of two biocompatible fluid or agent reservoirs 70 and 72 connectable to inlets 53 and 66 of device 50 of FIGS. 5–7. The reservoirs are defined by syringe barrels including Luer lock fittings 74 and 76, respectively, that mate with Luer lock connections 55 and 68 of device 50. The barrels each include a piston, or septum 78 and 80, respectively, as defined above. The septa separate the barrels into distal portions 82 and 84, respectively, containing biocompatible agent, and proximal portions 86 and 88, respectively, that are free of biocompatible agent. The proximal ends of the syringes are fastened to two syringe barrel pressurization adapters 22 and 90, respectively, each of which is connected to tubing 92. Tubing 92 is connectable, via conventional conduits and connections that are not shown, to a source of pressurized gas that fills regions 86 and 88 of reservoirs 70 and 72, respectively, in locations proximal to septa 78 and 80. Gas pressure supplied via tubing 92 drives biocompatible agent in distal regions 82 and 84 of the reservoirs into the device. Tubing 92 can be connected to any source of gas acceptable for use and, in preferred embodiments, is connected to the same source of medical gas to which gas conduits 40' and 40" are ultimately connected.

In operation, with reference to all figures, a source of an acceptable medical gas under pressure is connected to connector 1 of control box 10. Acceptable conventional tubing (not shown) connects gas outlet 8 of controller 10 to nipple 30 which defines the inlet to pressurize gas space 40 of device 50. Tubing (not shown) also connects outlet 7 of control box 10 with tubing 92 connected to reservoirs 70 and 72, supplying gas pressure to regions 86 and 88, respectively, of the reservoirs. Reservoirs 70 and 72 are connected via Luer connections 74 and 76, respectively, to Luer connections 53 and 66, respectively, of device 50. The control box can be replaced with a regulator, with a manifold and valves carried on the device for convenient access.

Operation can be carried out in a variety of modes, as will be readily apparent by those of ordinary skill in the art. In one preferred mode, toggles 5 and 6 initially are in "off" and "leak" settings, respectively. In these settings regions 86 and 88 of the reservoirs are not pressurized, and a first, low-pressure stream of gas is supplied to gas pressure space 40 and emerges continuously from gas conduits 40' and 40" of the device. Gas pressure in the "leak" setting is sufficient to remove any residual fluid from the distal ends of fluid conduits 34 and 29 remaining after application of fluid, to prevent accumulation of drip or drool of the material on the end of the device. To apply biocompatible fluid to a tissue surface, toggles 5 and 6 are switched to their "on" positions, resulting in pressurization of regions 86 and 88 of the reservoirs sufficient to drive biocompatible material from the reservoirs into the device and ultimately from the fluid outlets of the device. Gas pressure applied to gas conduit 60 which supplies gas pressure space 40 also is increased from the "leak", or low level, to a higher level of pressure and flow sufficient to spray biocompatible fluid delivered through conduits 29 and 34 onto a tissue surface. The exact value of these flow rates depends on the details of construction of the device, particularly the diameter of tubes leading to the outlets, and on the properties of the liquids, particularly their viscosity. Appropriate rates are readily determined by a combination of calculation and routine experimentation, as is done for fluid delivery devices in general. At a high gas flow rate, the liquid or liquids being expressed are entrained into the gas stream and carried to the surface being coated, as a spray or stream. The lower, "leak" gas flow rate continues to flow through the device even when it is intended that liquid not be expressed from the outlets. It is often observed that droplets of liquid may accumulate at outlets of similar devices. When the components of the liquids are reactive, then a coating may form on or in the outlets, and thereby plug the device. The "leak" flow rate of gas is selected to remove any droplets which may form at the outlets from the device, so that plugging does not occur. This greatly improves the reliability of the device, especially for repeated or intermittent use during a medical procedure. It also make the device easier to clean.

In some embodiments valve 62 and valve actuator 64 associated with the gas supply conduit and gas pressure space 40 is absent and switching toggle 6 from "leak" to "on" results in gas pressure exiting gas conduits 40' and 40" at a high, spray-producing level continuously. Biocompatible material then is sprayed onto a tissue surface by opening one or both of valves 57 and 66 thereby allowing material to exit conduits 29 and 34, respectively, and to be entrained in gas flow exiting gas conduits 40' and 40" and sprayed onto tissue. Thus, spraying and halting spraying is carried out simply by opening and closing valves 57 and 66 via valve actuator 25 and another actuator (not shown).

In embodiments where valve 62 is present, valve 62 can include a partially-closed, "leak" setting, and an open setting. When it is desirable to spray material onto a tissue surface valve 62 can be switched from the "leak" to the "open" position and then, or simultaneously, one or more of valves 57 and 66 can be opened to deliver biocompatible fluid from the outlets of conduits 29 and 34. When it is desirable to cease spraying, valves 57 and/or 66 are closed and valve 62 is returned to the "leak", lower-pressure setting where gas exits conduits 40' and 40" at levels sufficient to clear the outlets of conduits 34 and 29 of any excess material to prevent accumulation of drip or drool. Operation of any of valves 62, 57, and 66 can be linked together such that depression or switching of a single actuator changes settings of two or more valves simultaneously. For example, where it is desirable to spray fluid from conduits 29 and 34 simultaneously onto a tissue surface, one actuator can be linked to all of valves 62, 57, and 66 such that switching of the single actuator from a first position to a second position opens valves 57 and 66, allowing biocompatible fluid flow, and simultaneously switches gas pressure from "leak" to "on" to spray the fluid onto a tissue surface. Switching the lever back to the first position closes valves 57 and 66 and returns valves 62 to the "leak" position where gas flows from the gas conduits at a lower rate to clear the device of excess fluid. In this embodiment, toggle 6 can simply be an on/off switch, the "on" setting supplying gas at spray value, and spray versus leak gas pressure values being regulated by valve 62.

In some embodiments it is desirable to apply material to a tissue surface and then effect a change in the material by exposing the material to an energy source such as electromagnetic radiation, for example light. For example, a photopolymerizable polymeric material, as known in the art and described in U.S. patents and international patent publication referenced above, can be delivered from one or both of conduits 29 and 34 onto a tissue surface, and then exposed to light to polymerize the material. In such an embodiment the device can be equipped with an emitter 96 of electromagnetic radiation. As illustrated, emitter 96 is an annular emitter surrounding the distal tip of the device. The emitter is connected via an electronic connection, an optical fiber, waveguide or other conduit, or the like to a source of electromagnetic radiation or a source of energy (not shown). Suitable emitters, in combination with suitable material that is effected by electromagnetic radiation emission, are known, as described in the above-referenced documents.

Several parameters and components of the invention will now be described in greater detail, with alternatives.

Liquid Ports and their Attached Reservoirs and Sources

This device is designed to control the flow of at least two different liquids in their delivery to a tissue surface. The liquids, which may be of any viscosity, are provided through at least two ports, which may be of any suitable design. Design parameters for ports include the ability to make a reversible sterile or aseptic connection to the port, and wherein the connection is resistant to disconnecting under the pressures applied to the device, such as 15 to 100 pounds per square inch (psi), typically about 10 to 30 PSI. The device is preferably designed to allow the liquid-contacting portion of the device to be separated from the rest of the device, so that the liquid-contacting portion of the device is disposable.

A preferred reservoir is a syringe. The syringe will typically be mounted on or in the body of the device through a port having a widely used connection means, such as a Luer taper. Any conventional locking arrangement is suitable, including a "Luer-Lock" or other twist connection, and/or a pressurization arrangement as described herein, which will force the syringe barrel into the port under gas pressure.

An alternative reservoir is a closable bag with an opening which mates with the port in the body. A Luer taper connection on the bag is a suitable mating arrangement, with locking or pressure retention as for a syringe. The bag may be contained in a cylindrical tube or other container which allows the application of gas pressure to the bag.

Alternatively, one or more of the fluids may be supplied from an external source, such as a pressurized canister, which can provide more pressurizable fluid than can be conveniently contained in a reservoir mounted on the device. In this case, the source will be connected to the device by liquid-carrying lines connected to the ports of the device.

Gas Sources and Pressurization

Any medically acceptable gas can be used for pressurization of the device and for providing a gas flow at the liquid outlets, including the readily available gasses carbon dioxide, nitrogen, and compressed air. The gas should meet medical standards for sterility and similar parameters. It is desirable to filter the gas before it enters the apparatus, to ensure sterility and for prevention of particulate contamination. Filters (not shown) can be provided in conduits shown in the figures. The gas may be humidified. The pressure at which the gas is available to the delivery device is normally regulated to a fixed value at the gas source. Gas pressure within the device is provided to drive gas flow through annuli at the liquid outlets. Variable pressure is provided within the device so that each of a low flow rate and a high flow rate can be obtained. Any means of selective pressure variation is suitable. Since the gas is normally flowing in the device, the simplest means of flow regulation is by a valve, or by any reversible means of narrowing or closing the passage through which the gas flows.

Gas pressure is also optionally provided to drive the liquids being applied through the liquid outlets. In the case of a syringe as reservoir, the syringe can have its plunger replaced with a moveable septum or a piston, and the syringe can be connected, at the end which would normally accept the plunger, to a source of pressurized gas. For example, one could use a pressure adapter assembly which locks onto the flanges of the syringe. Such adapters are commercially available, for example from EFD of East Providence, R.I., USA. Other devices and arrangements are known, and similar arrangements would be used for a bag-type reservoir, or a separate source. The pressure adapter is connected to the gas source upstream of whatever restriction serves to allow the self-cleaning gas flow (described further below), and also upstream of the valve regulating the higher delivery or spraying flow, as described in more detail below. Gas pressure below the valve is always less than the pressure at the top of the syringe, allowing a liquid to be forced through the outlet when its valve is open. Pressure in the syringes or other reservoirs can also be provided by a separate gas pressure source, or a mechanical device, or hand pressure.

Device Outlets

The device will have at least one, and in most embodiments two, fluid outlets. Each outlet is in communication with at least one inlet which is connected to a reservoir or source of fluid. Each fluid which is reactive will have a separate fluid path from any liquid with which it would react while in the device. In the simplest case, there are two reservoirs, each connected to a separate outlet. In more complex arrangements, there may be multiple reservoirs. These may contain additional reactive components, in which case the design will allow for their segregation; or they may be secondary reservoirs, which contain non-reactive components, such as drugs and other biologically active agents, or excipients. These secondary reservoirs may be passively linked to one of the active component reservoirs and dispensed with that component, and so may not require additional outlets or valves. Such secondary reservoirs are not included in requirements for providing separate valves and outlets for each reservoir.

At each fluid outlet, flowing gas is provided through an opening which preferably is substantially annular with respect to the liquid outlet. The annular configuration (the gas annulus, or gas outlet) allows flowing gas to sheathe the outlet and thereby entrain the liquid and deliver it to a tissue surface. This will typically result in a spray, although in many cases the exact droplet size of the entrained liquid will not be critical. As used herein, "spray" means fluid carried from an outlet of a device of the invention to a tissue surface via pressurized gas provided by the device, and is independent of droplet size or the existence of droplets. Gas flow through the gas annulus is provided at two flow levels. A higher flow rate is used to deliver the liquid, while a lower flow rate is used to remove any liquid which may accumulate at the outlet through leakage, relaxation effects, or the like. This continuously self-cleaning feature prevents reaction of the two different liquids while in or on the device, and thereby prevents the device from becoming plugged during a medical or surgical procedure.

The importance of self-cleaning is made evident by comparison with non-self cleaning devices in the art for dispensing two-component reactive fluids. These are supplied with multiple final fluid outlet assemblies, so that the outlet assembly can be changed when it clogs during the application procedure. Such changes always increase the complexity, cost, and risk of infection, and are especially undesirable when the application of the fluids is being done through a minimally invasive portal, such as the cannula of a trocar, or via a catheter.

The gas sheathing of the liquid flow is preferably provided by a substantially annular gas outlet surrounding each liquid outlet. Surrounding more than one liquid outlet with a single gas outlet annulus is a less desirable solution, because the risk of mixing of reactive liquids from the outlets, which can cause clogging, is increased.

The gas annulus can be constructed in any convenient way, and several are known in the art. When the outlet and the gas are flowing through concentric tubes, then, if the tubing is rigid, it can be fixed at any point to maintain a substantially annular spacing. In an alternative design, liquid flows in tubes through a pressurized gas space and exits though the ends of the tubes, each of which is substantially concentric with an opening in the end of the device, the opening having a larger diameter than the tube. The location of the inner, liquid-containing tube can be maintained by intrinsic tube rigidity, or by insertion of spacers between the tube and the opening at points on the tube's circumference. In another design, which can be inexpensive, a gas-carrying tube and a liquid-carrying tube, with connecting webs as required, are made in one piece by extrusion, as is commonly done in the manufacture of catheters and as described in U.S. Pat. No. 5,665,867 (Linder). The continuous extruded tubing is cut to length, fitted with adapters if required, and connected to sources of gas and liquid. For ease of handling, the tubes may bound together or placed in a common housing.

Because of the continuous cleaning of the outlets by the gas flow from the annuli, it is not necessary in the devices of the invention to have the liquid outlets protrude beyond the annuli, in contrast to prior art devices such as those of U.S. Pat. No. 5,582,596. This allows simplification of the construction of the device, for example by the use of extruded tubing.

Valving and Flow Control

At least three fluid streams within the device in preferred embodiments require control: the two liquids, and the gas flow. The required valves are preferably mounted on the device, but may be mounted on an separate control box, or at the sources of the fluid. At least two valves are required in preferred embodiments, and three are preferred. In the two valve arrangement, each valve when opened admits both liquid and sheathing gas into a path leading to one of the liquid outlets. (The background gas flow required for self-cleaning is presumed to be always "on" when the device is connected to a gas supply.) In a mechanically simpler arrangement, each fluid has a valve, and the gas stream is separately valved and supplies both liquid outlets simultaneously at either the self-cleaning rate or the higher spraying or delivery rate.

Any type of valve is potentially suitable in this application. Preferred valves for liquid are described as "momentary-contact, normally closed", in which the valve is open only while it is being pressed on or otherwise actuated. Such valves include pinch-clamps, "trumpet"-type valves, and ordinary spring-return push button gas valves. Also useful are pinch valves, pinch valves with pre-use kink-preventers, stopcock valves, and "duck-bill" valves (slit in plug in tube opens with compression along the length direction of the slit). Gas valves, when separate, preferably have two or more discrete positions, so that the gas flow can be increased from the low flow rate, self-cleaning level to a higher level for spraying or fluid delivery. Preferably, the gas flow valve will remain at either position until changed to the other. Examples of useful gas valves include a toggle switch and a slide valve, and any valve which can be switched between two positions can be used. The self-cleaning flow can be provided in any convenient way, and may either pass through the same valve as the high flow rate flow, or may have a separate supply passage. A simple and preferred method is to provide a controlled leak in the gas control valve, so that in the low-flow or "spray off" position, some gas continues to flow through the valve. An alternative method is to provide one or more separate passages between the gas source and the gas annulus outlets, with a flow restriction (narrowing) in the passage(s) to provide a steady background flow. An adjustable needle valve is useful in such an arrangement.

The valves may be linked or not linked, depending on the particular intended method of use. When the two reactive liquids should be dispersed sequentially, it is convenient to link the liquid-dispensing valves with a rocker switch, so that only one dispensing valve can be opened at a given time. A controlling toggle or other two-position switch can also be used for this purpose.

Alternatively, it is desirable with some coating systems, such as ionic coacervates as described below, to require simultaneous dispensing of the two reactive components. In this case, activation of both outlets can be controlled by any convenient means of interlocking the switches.

In addition, it is in some cases preferable to give the operator control over the dispensing of the individual reagents, in which case no interlock is provided.

Although the valves have been described in terms of manual operation, they may also be operated by electrical or pneumatic means, or controlled by electronic contacts. The electronic contacts can be operated manually, or may be interfaced with a computer or dedicated electronic device.

Reaction Activation

The two or more reactive fluids dispensed by the device may be spontaneously reactive, so that a polymerized, crosslinked, precipitated or otherwise solidified coating is formed without further intervention. However, it may be desirable to initiate or accelerate a chemical reaction by provision of energy to the polymers on the tissue. Examples of such energy are electromagnetic waves, such as microwave, infrared, visible, and ultraviolet frequencies. Heated gas is another possible source of activating energy.

The energy may be provided by a source separate from the device; or a conduit for energy delivery may be included in the device. In the simplest embodiment, the conduit, such as a pipe for gas or an optical fiber for light, could be attached to the outside of the device. For minimally invasive uses of the device, in particular, it could be advantageous to incorporate the energy-delivery conduit into the body of the device, preferably with an outlet for the energy at or near the distal end of the device (i.e., the end closest to the patient).

Materials for the Coating

Any two-component liquid tissue coating can be dispensed with the device, including those described in U.S. Pat. Nos. 5,749,968 and 5,800,373 and international patent publication no. WO 96/29370, which are hereby incorporated by reference. These include the free-radical polymerizable coating described above, for which the alternating application method is preferred. Two-component systems can also be made from components A containing amine or hydroxyl groups and components B containing isocyanate, dialdehyde, polyaldehyde, polyphenol or epoxy groups, in which A and B react to form covalent crosslinks on contact. Catalysts or accelerators may be included in the formulation as required.

Other reactive coatings are formed by the coacervation of oppositely charged polymers. In this case A is a polyanion and B is a polycation; for example, A could be alginate and B polylysine or chitosan. In a variant of this, certain ionic polymers, such as alginate, can be gelled by the addition of specific small molecules or ions, such as calcium ions. Then A could be alginate and B a solution of calcium ions.

Either or both of the reactive components A and B may comprise a polymeric backbone. The backbone may be made of any polymer which is acceptable in the particular medical use. Such polymers are preferably biocompatible, wherein no sustained or excalating inflammatory response is elicited. In most cases, it is preferably that the polymer be biodegradable, or that the polymer be linked to the coating by biodegradable linkages, and itself be secreted from the body. Biodegradable linkages include esters, especially of hydroxy acids; amides; anhydrides; and other labile linkages known in the art. Synthetic polymers are preferred. However, the polymer may comprise a natural polymer, such as fibrinogen, or a synthetic derivative of a natural polymer, such as an acrylated polysaccharide. A typical preferred polymer mixture will be predominantly synthetic, but make contain some proportion of unmodified natural polymers, such a 20%, while being described as predominantly synthetic. Natural polymers which have been chemically altered are not considered to be identical with natural polymers. Natural polymers included for their effects as biologically active materials are not considered to be part of the coating polymers unless otherwise stated.

Still other reactive coatings are formed by the action of enzymes on substrates. Fibrin sealant is a well-known example of such a coating. Other reactive coatings can be formed by the binding of the members of a binding pair. A well-known pair, suitable for creating coatings, is biotin conjugated to a polymer, plus the protein avidin, optionally conjugated to a polymer. Similarly, the binding of antibodies to polyvalent antigens can form a coating.

In addition to the reactive components, other materials may be incorporated into the coating during its application. These include biologically active molecules, including conventional small-molecule organic drugs, proteins and peptides, nucleic acids, polysaccharides and inorganic materials. The proteins can be, among others, enzymes, growth factors, growth inhibitors, antibodies, cell attachment modulators, and immune system modulators.

Uses

The device may be used to create coatings useful in the treatment of any medical condition where such a coating is useful. Such conditions include without limitation: prevention of adhesions, sealing of leaks of bodily fluids or air, sealing of anastamoses, staple lines and suture lines, coating of surfaces to protect them, for example, from friction or exposure to air, adhering tissue together or adhering tissue to an implant, formation of implants for delivery of drugs or cells, or for mechanical support, and dressing of external and internal wounds.

EXAMPLE 1

A device according to the invention was constructed to establish that the device worked as intended and was suitable for creating tissue coatings. The arrangement allows simple changes in system design and operating parameters to be tested easily, to establish appropriate conditions for a device designed for high volume production.

The entire system contained a control box, shown in FIG. 1, and the application device, shown in FIG. 2 and in detail in FIGS. 3 and 4. The smaller tube carried "primer", a low viscosity fluid containing about 30% reactive synthetic macromer and certain initiators of polymerization, which was applied in small amounts to the tissue or other surface. The larger tubes carried "sealant", which contained about 20% of a reactive macromer of higher molecular weight, as well as initiators, and the sealant material had higher viscosity. It also was applied in two to three times the volume of the primer, to build up a thicker layer of hydrogel having suitable mechanical properties.

After adjustment of pressures and low flow rates to obtain optimal spraying and self-cleaning with the particular macromer solutions being tested, the device was used to deposit primer and sealer sequentially on a test substrate, while illuminating the sprayed area with blue-green light at about 100 mW per square cm. A coating of appropriate properties was obtained. Using a similar device, in which the nozzle housing assembly had been sterilized, a coating was deposited on living tissue, and a satisfactory coating was also obtained.

Those skilled in the art would readily appreciate that all parameters listed herein are meant to be exemplary and that actual parameters will depend upon the specific application for which the methods and apparatus of the present invention are used. It is, therefore, to be understood that the foregoing embodiments are presented by way of example only and that, within the scope of the appended claims and equivalents thereto, the invention may be practiced otherwise than as specifically described.

What is claimed is:

1. A device for applying a biocompatible agent to a tissue surface, comprising:
   a housing having a biocompatible agent conduit connectable to a source of a biocompatible agent, the conduit including a biocompatible agent outlet adapted to emit a biocompatible agent;
   a gas conduit associated with the housing, connectable to a source of a pressurized medical gas and having an outlet adapted to emit pressurized medical gas in an orientation carrying biocompatible agent from the biocompatible agent outlet to a tissue surface; and
   a gas regulator adapted to provide medical gas to the outlet of the gas conduit at at least two predetermined positive gas pressures,
   wherein the at least two predetermined gas pressures include a first predetermined gas pressure sufficient to carry a biocompatible agent from the biocompatible agent outlet to the tissue surface, and a second predetermined gas pressure less than the first pressure, sufficient to clear residual biocompatible agent from the biocompatible agent outlet.

2. A device as in claim 1, comprising a port connectable to a reservoir of a biocompatible agent and fluidly connected to the biocompatible agent conduit.

3. A device as in claim 1, further comprising a valve associated with the biocompatible agent conduit switchable from a closed conduit position to an open conduit position.

4. A device as in claim 1, wherein the gas regulator is a valve associated with the gas conduit.

5. A device as in claim 1, wherein the gas regulator is associated with a controller remoter from the device.

6. A device as in claim 1, further comprising a biocompatible agent valve associated with the biocompatible agent conduit switchable from a closed conduit position to an open conduit position, wherein the gas regulator is a gas valve associated with the gas conduit and the biocompatible agent conduit and the gas conduit are together switchable with a single actuator.

7. A device as in claim 1, comprising at least two ports connectable to at least two separate reservoirs each containing a biocompatible agent, each port fluidly connected to a biocompatible agent conduit including a biocompatible agent outlet adapted to emit a biocompatible agent.

8. A device as in claim 1, comprising at least two ports connectable to at least two separate reservoirs of biocompatible agent and including first and second biocompatible agent outlets, respectively, and at least two gas conduits associated with the housing, each connectable to a source of a medical gas and having a gas outlet adapted to emit pressurized medical gas in an orientation carrying biocompatible agent from a biocompatible agent outlet to a tissue surface.

9. A device as in claim 1, comprising at least two ports connectable to at least two separate reservoirs of biocompatible agent, each port fluidly connected to a conduit including a biocompatible agent outlet adapted to emit a biocompatible agent in an orientation allowing medical gas emitted form the outlet of the gas conduit to carry biocompatible agent to the tissue surface.

10. A device as in claim 1, further comprising at least two separate reservoirs of biocompatible agent, and at least two ports connectable to the at least two separate reservoirs of biocompatible agent, each port fluidly connected to a separate biocompatible agent conduit including a separate outlet.

11. A device as in claim 10, wherein each of the at least two separate reservoirs is connectable to a source of pressurized gas.

12. A device as in claim 10, wherein each of the at least two separate reservoirs is connectable to the source of pressurized medical gas to which the gas conduit is connectable.

13. A device as in claim 12, further comprising a source of medical gas at a pressure greater than atmospheric pressure connected to the gas conduit and connected to the at least two separate reservoirs.

14. A device as in claim 10, wherein the at least two separate reservoirs of biocompatible agent comprise at least two agents that, when mixed, chemically react to form a tissue coating.

15. A device as in claim 14, wherein at least one of the at least two agents comprises a synthetic polymer.

16. A device as in claim 14, wherein each of the at least two agents comprises a synthetic polymer.

17. A device as in claim 14, wherein each of the at least two agents consists essentially of a synthetic polymer.

18. A device as in claim 1, further comprising a source of medical gas at a pressure greater than atmospheric pressure connected to the gas conduit.

19. A device as in claim 18, further comprising a reservoir of a biocompatible agent connected to the biocompatible agent conduit and connected to the source of pressurized medical gas.

20. A device as in claim 1, further comprising a source of medical gas at a pressure greater than atmospheric pressure, and at least one reservoir of biocompatible agent.

21. A device as in claim 1, further comprising an emitter of energy mounted so as to direct energy at biocompatible agent that has been conveyed from the biocompatible agent outlet onto a tissue surface.

22. A device as in claim 1, further comprising at least two separate reservoirs of biocompatible agent mounted on the device, a source of medical gas at a pressure greater than atmospheric pressure, at least two ports connected to the at least two separate reservoirs of biocompatible agent each fluidly connected to a separate biocompatible agent conduit including a separate outlet adapted to emit biocompatible agent to a tissue surface, and at least two gas conduits each connected to the source of pressurized medical gas and having an outlet adapted to emit pressurized medical gas in an orientation carrying biocompatible agent from the outlet of a biocompatible agent conduit to a tissue surface.

23. A device as in claim 22, wherein the at least two predetermined gas pressures include a first predetermined gas pressure sufficient to carry a biocompatible agent from the biocompatible agent outlet to the tissue surface, and a second predetermined gas pressure less than the first pressure, sufficient to clear residual biocompatible agent from the biocompatible agent outlet.

24. A device as in claim 23, wherein each of the at least two separate reservoirs is connected to a source of gas at a pressure greater than atmospheric pressure.

25. A device as in claim 24, wherein each of the at least two separate reservoirs is connected to the source of pressurized medical gas to which the at least two gas conduits are connected.

26. A device as in claim 25, further comprising an emitter of energy mounted so as to direct energy at biocompatible agent emitted from a biocompatible agent outlet to a tissue surface.

27. A device as in claim 26, wherein the at least two separate reservoirs of biocompatible agent comprise at least two agents that, when mixed, chemically react to form a tissue coating.

28. A device as in claim 26, wherein at least one of the at least two agents comprises a synthetic polymer.

29. A device for applying a biocompatible agent to a tissue surface, comprising:
a housing having at least two biocompatible agent conduits each connectable to a source of a biocompatible agent and each including a biocompatible agent outlet adapted to emit a biocompatible agent;
at least two gas conduits associated with the housing, each connectable to a source of a medical gas at a pressure greater than atmospheric pressure and each having a separate gas outlet associated with one of the at least two biocompatible agent outlets, adapted to emit pressurized medical gas in an orientation carrying biocompatible agent from a biocompatible agent outlet to a tissue surface,
wherein the at least two biocompatible agent outlets and the at least two gas outlets define together at least two agent/gas delivery outlets flush with a surrounding surface of the device defining a planar area greater than at least twice the cross sectional area of the agent/gas delivery outlets.

30. A device for the application of a coating to a tissue surface of a patient, wherein the device comprises:
a fluid inlet port configured to connect to a source of a fluid;
a gas inlet port configured to connect to a source of pressurized medical gas;
a fluid delivery outlet, and a fluid conduit fluidly connecting the fluid delivery outlet with the fluid inlet port;
a valve associated with the fluid conduit able to regulate the outflow of fluid from the fluid delivery outlet;
a gas outlet proximate the fluid delivery outlet, and a gas conduit fluidly connecting the gas outlet with the gas port; and
means for regulating the rate of gas flow through the gas outlet wherein, while said device is in operation and in a fluid delivery off setting, gas flow is maintained at a flow level sufficient to remove any fluid present at the fluid delivery outlet.

31. A device as in claim 30, comprising:
at least two fluid inlet ports configured to connect to at least two sources of fluid;
a source of medical gas at a pressure greater than atmospheric pressure;
at least two fluid delivery outlets, and fluid conduits fluidly connecting the fluid delivery outlets with the fluid inlet ports;
at least two valves associated with the fluid conduits each able to regulate the outflow of fluid from a fluid delivery outlet;
an annular gas outlet proximate each fluid delivery outlet; and
means for regulating the rate of gas flow through the annuli wherein, while said device is in operation, gas flow is maintained at a flow level sufficient to remove any fluid present at the fluid delivery outlets.

32. A device as in claim 31, further comprising at least two sources of fluid, wherein components of each of the at least two fluids chemically react upon mixing.

33. A device as in claim 32, wherein at least one of the reactive components comprises a synthetic polymer.

34. A device as in claim 33, wherein each reactive component comprises a synthetic polymer.

35. A device as in claim 33, wherein each reactive component consists essentially of a synthetic polymer.

36. A device as in claim 31, wherein each of the fluid delivery outlets defines a separate annulus.

37. A device as in claim 31, further comprising at least two reservoirs of biocompatible fluid mounted by the device connected to the at least two fluid inlet ports, respectively, and connected to the source of medical gas.

38. A device as in claim 37, wherein the at least two reservoirs of biocompatible fluid mounted by the device are at least two syringe barrels each including a septum slidably disposed in the barrel, the barrel connected to the source of medical gas.

39. A device as in claim 37, wherein the at least two biocompatible fluids chemically react upon mixing.

40. A device as in claim 37, wherein each of the fluid delivery outlets defines a separate annulus, and the annular gas outlet proximate each fluid delivery outlet surrounds a fluid delivery outlet and defines a substantially annular, coaxial fluid/gas delivery outlet that is flush with a surrounding surface of the device defining a planar area greater than at least twice the cross sectional area of the fluid/gas delivery outlet.

41. A device as in claim 37, further comprising a conduit associated with the device for transmitting energy to fluid delivered from the fluid delivery outlet.

42. A device as in claim 30, further comprising a source of fluid at a pressure greater than atmospheric pressure connectable to the fluid inlet port.

43. A device as in claim 42, wherein the source of fluid is a reservoir mounted on the device.

44. A device as in claim 42, comprising at least one biologically active material in the source of fluid.

45. A device as in claim 42, wherein the source of fluid forms a coating on living tissue for the treatment of a medical condition.

46. A device as in claim 30, further comprising a source of fluid that is a reservoir mounted on the device.

47. A device as in claim 30, wherein the gas outlet surrounds the fluid delivery outlet and the fluid delivery outlet does not protrude substantially beyond the gas outlet.

48. A device as in claim 30, wherein the fluid delivery outlet is surrounded by a surface of the device and does not protrude substantially from the surface.

49. A device as in claim 48, wherein the fluid delivery outlet is flush with the surface.

50. A device as in claim 30, further comprising a source of fluid that is a syringe barrel including a septum slidably disposed in the barrel.

51. A device as in claim 30, further comprising a source of fluid that is a syringe barrel including a septum slidably disposed in the barrel, wherein the barrel is connectable to a source of pressure greater than atmospheric pressure.

52. A device as in claim 51, wherein the source of fluid is a syringe barrel mounted on the device.

53. A device as in claim 30, further comprising a conduit associated with the device for transmitting energy to fluid delivered from the fluid delivery outlet.

54. The use of the device of claim 30 for the treatment of a medical condition.

55. The use of claim 54, wherein the treatment comprises prevention of adhesions; sealing of leaks of bodily fluids or air; sealing of anastamoses, staple lines and suture lines; coating surfaces to protect them; adhering tissues together or adhering tissue to an implant; formation of implants for delivery of drugs or cells, or for mechanical support; and dressing of external and internal wounds.

56. A device as in claim 30, comprising:
- at least two fluid inlet ports configured to connect to at least two sources of fluid;
- a source of medical gas at a pressure greater than atmospheric pressure;
- at least two fluid delivery outlets, and fluid conduits fluidly connecting the fluid delivery outlets with the fluid inlet ports;
- at least two valves associated with the fluid conduits each able to regulate the outflow of fluid from the fluid delivery outlet;
- an annular gas outlet proximate each fluid delivery outlet; and
- means for regulating the rate of gas flow through the annular gas outlet wherein, while said device is in operation, gas flow is maintained at a flow level sufficient to remove any fluid present at the fluid delivery outlets.

57. A device as in claim 56, wherein each of the fluid delivery outlets defines a separate annulus.

58. A device for the application of a coating to a tissue surface of a patient, wherein the device comprises:
- at least two fluid inlet ports configured to connect to at least two sources of fluid;
- a gas inlet port configured to connect to a source of pressurized medical gas;
- at least two fluid delivery outlets, and fluid conduits fluidly connecting the fluid delivery outlets with the fluid inlet ports;
- at least two valves associated with the fluid conduits each able to regulate the outflow of fluid from a fluid delivery outlet;
- an annular gas outlet proximate each fluid delivery outlet, and a gas conduit fluidly connecting the annular gas outlet with the gas inlet port; and
- means for regulating the rate of gas flow through the annuli wherein, while said device is in operation, gas flow is maintained at a flow level sufficient to remove any fluid present at the fluid delivery outlets.

59. A device as in claim 58, wherein the annular gas outlet surrounds the at least two fluid delivery outlets and the at least two fluid delivery outlets do not protrude substantially beyond the annular gas outlet.

60. A device as in claim 58, wherein the at least two fluid delivery outlets is surrounded by a surface of the device and does not protrude substantially from the surface.

61. A device as in claim 60, wherein the at least two fluid delivery outlets are flush with the surface.

62. A device for the application of a coating to a tissue surface of a patient, wherein the device comprises:
- a fluid inlet port configured to connect to a source of a fluid;
- a gas inlet port configured to connect to a source of pressurized medical gas;
- a fluid delivery outlet, and a fluid conduit fluidly connecting the fluid delivery outlet with the fluid inlet port;
- a valve associated with the fluid conduit able to regulate the outflow of fluid from the fluid delivery outlet;
- a gas outlet proximate the fluid delivery outlet, and a gas conduit fluidly connecting the gas outlet with the gas port; and
- means for regulating the rate of gas flow through the gas outlet wherein, while said device is in operation, gas flow is maintained at a flow level sufficient to remove any fluid present at the fluid delivery outlet,
- wherein the fluid delivery outlet is surrounded by a surface of the device and is flush with the surface.

* * * * *